(12) United States Patent
Paarhammer et al.

(10) Patent No.: US 12,355,290 B2
(45) Date of Patent: Jul. 8, 2025

(54) MATRIX BATTERY SYSTEM FOR MEDICAL DEVICES

(71) Applicant: GE Precision Healthcare LLC, Wauwatosa, WI (US)

(72) Inventors: Markus Paarhammer, Oberwang (AT); Franz Steinbacher, Vöcklamarkt (AT)

(73) Assignee: GE Precision Healthcare LLC, Wauwatosa, WI (US)

( * ) Notice: Subject to any disclaimer, the term of this patent is extended or adjusted under 35 U.S.C. 154(b) by 1244 days.

(21) Appl. No.: 16/951,063

(22) Filed: Nov. 18, 2020

(65) Prior Publication Data
US 2022/0158469 A1    May 19, 2022

(51) Int. Cl.
| | | |
|---|---|---|
| *H02J 7/00* | (2006.01) | |
| *H02M 3/04* | (2006.01) | |
| *A61B 5/055* | (2006.01) | |
| *A61B 6/00* | (2006.01) | |
| *A61B 8/00* | (2006.01) | |

(52) U.S. Cl.
CPC ........ *H02J 7/00714* (2020.01); *H02J 7/0013* (2013.01); *H02J 7/0047* (2013.01); *H02M 3/04* (2013.01); *A61B 5/055* (2013.01); *A61B 6/56* (2013.01); *A61B 8/56* (2013.01)

(58) Field of Classification Search
CPC .... H02J 7/0013; H02J 7/0047; H02J 7/00714; H02M 3/04; A61B 5/055; A61B 6/56; A61B 8/56
USPC .......................................................... 363/17
See application file for complete search history.

(56) References Cited

U.S. PATENT DOCUMENTS

| | | | |
|---|---|---|---|
| 9,391,532 B2 * | 7/2016 | Reiter ..................... | H02M 1/10 |
| 2005/0156566 A1 * | 7/2005 | Thorsoe .............. | H02J 7/00309 |
| | | | 320/116 |
| 2010/0207579 A1 * | 8/2010 | Lee ........................ | H02J 7/0018 |
| | | | 320/120 |

(Continued)

FOREIGN PATENT DOCUMENTS

WO    WO-03088446 A1 * 10/2003   ............ H02J 7/0019

OTHER PUBLICATIONS

Wilkie et al., "Integrated multilevel converter and battery management," SPEEDAM 2008 p. 756-759 (International Symposium on Power Electronics, Electrical Drives, Automation and Motion), 5 pages.

*Primary Examiner* — Yemane Mehari

(57) ABSTRACT

Systems and methods are provided for supplying an electrical power to a medical imaging system. The system comprises a primary power supply unit for providing an input electrical power. The system further comprises an H-bridge converter connected to the primary power supply unit and configured to receive an electrical power from the primary power supply unit. The system further comprises at least one battery line comprising one or more batteries. The at least one battery line is connected to the H-bridge converter and the H-bridge converter is configured to charge the one or more batteries of the at least one battery line using the input electrical power from the primary power supply unit. The system further comprises an output connected to the H-bridge converter and configured to supply the electrical power stored in the one or more batteries to the medical imaging system.

19 Claims, 3 Drawing Sheets

(56) References Cited

U.S. PATENT DOCUMENTS

2012/0086412 A1* 4/2012 Chimento .......... H02M 7/4835
                                                                                     323/207
2017/0085122 A1* 3/2017 Nasiri ...................... A61B 6/56

* cited by examiner

MATRIX BATTERY SYSTEM FOR MEDICAL DEVICES

FIELD OF THE INVENTION

Embodiments of the subject matter disclosed herein relate to medical imaging systems, and more particularly, to a matrix battery supported system for supplying power to the medical imaging systems.

BACKGROUND OF THE INVENTION

Various medical imaging systems and methods are used to obtain images of the affected regions of the subject for diagnosing the medical conditions of the subject. The medical imaging system may be for example, an ultrasound imaging system, an x-ray system, a computed tomography (CT) imaging system, a magnetic resonance imaging (MRI) system, a single photon emission computed tomography system, a positron emission tomography (PET) system or a multi-modal imaging system. These and other systems are the most widely known and used across the globe for acquiring the image data of the subject and generate user viewable images of the subject.

Imaging a subject using the medical imaging system such as a computed tomography (CT), or a magnetic resonance imaging (MRI) system involves positioning the subject over the table, moving the table inside the gantry of the imaging system. In case of the CT scan devices, the x-rays may be passed in different directions through the subject body to obtain the images of the internal volume of the subject. The CT-scan devices include an x-ray generator that powers the x-ray tube for emitting the x-rays on to the subject body positioned in the gantry and an x-ray detector is positioned to receive the x-rays. The x-rays received by the detector are processed using various image reconstruction and visualization techniques to generate a user viewable image of the subject. Although the total time taken for the CT-scan usually varies between thirty to forty-five minutes, the time of actual x-ray exposure varies between few seconds to few minutes. Highest power consumption often referred as the "peak power" or "peak load" is consumed during these few seconds of the x-ray dose and known systems require three-phase power supply to meet the peak power demand.

In magnetic resonance imaging (MRI) systems, once the subject is placed inside the gantry, a whole-body radiofrequency (RF) coil may be used for transmitting the waveform towards subject anatomy. The RF coil may be a surface coil. The surface coil containing receiving channels may be used for receiving the signals from the subject anatomy. Typical surface coil would have eight receiving channels; however, a different number of channels are possible. The received MR signals are demodulated, filtered, and digitized in the receiver section of the transceiver. The MR signals produced from excitation of the target are digitized by the transceiver module. The MR system control then processes the digitized signals by Fourier transform to produce k-space data, which is transferred to a memory module or other computer readable media, via the MRI system control to generate a user viewable image of the subject.

Other imaging systems such as an x-ray or an ultrasound may be static or portable systems that may be powered to obtain the image data from the subject body. Supplying electrical power to the medical imaging system requires electrical and electronics infrastructure, and a power backup for uninterrupted imaging. Different systems and methods are available for supplying the peak power or supplying the backup power that promise uninterruptible power supply (UPS) critical for the medical imaging systems. However, these "back-up" systems require separate charging lines and discharging lines for charging the batteries and powering the medical imaging devices respectively.

Further, the lithium-ion batteries that are currently being used to power the medical systems have maximum capacity of less than one hundred watt-hour of power supply capacity due to the air fright shipping regulations and multiple such batteries need to be combined to derive the higher power. In the existing power backup systems, the batteries need to be physically connected/disconnected to ramp up or scale down the power supply and the process is time consuming. Therefore, it is challenging to provide a higher amount of power using the existing batteries.

Accordingly, there is a need for a system that will reduce the power infrastructure required for charging/discharging the batteries and allow combining several batteries based on the power requirement of the medical imaging system.

SUMMARY OF THE INVENTION

This summary introduces concepts that are described in more detail in the detailed description. It should not be used to identify essential features of the claimed subject matter, nor to limit the scope of the claimed subject matter. Its sole purpose is to present concepts in a simplified form as a prelude to the more detailed description that is presented later.

In accordance with an aspect of the disclosure a system for supplying an electrical power to a medical imaging system is provided. The system comprises a primary power supply unit for providing an input power. The system further comprises an H-bridge converter connected to the primary power supply unit and configured to receive the electrical power from the primary power supply unit. The system further comprises at least one battery line comprising one or more batteries. The at least one battery line is connected to the H-bridge converter and the H-bridge converter is configured to charge the one or more batteries of the at least one battery line. The system further comprises an output connected to the H-bridge converter and configured to supply the electrical power stored in the one or more batteries to the medical imaging system through the H-bridge converter.

In accordance with an aspect of the disclosure, a method for supplying an electrical power to a medical imaging system is provided. The method comprises supplying an electrical power for charging one or more batteries connected to the at least one battery line through an H-bridge converter. The method further comprises connecting the one or more batteries of the at least one battery line to an output through the H-bridge converter. The method further comprises supplying the electrical power from the output to the medical imaging system using the electrical power stored in the one or more batteries.

DETAILED DESCRIPTION

In the following specification and the claims, reference will be made to a number of terms, which shall be defined to have the following meanings.

The singular forms "a", "an", and "the" include plural references unless the context clearly dictates otherwise.

As used herein, the terms "software" and "firmware" are interchangeable and include any computer program stored in memory for execution by devices that include, without limitation, mobile devices, clusters, personal computers, workstations, clients, and servers.

As used herein, the term "computer" and related terms, e.g., "computing device", "computer system" "processor", "controller" are not limited to integrated circuits referred to in the art as a computer, but broadly refers to at least one microcontroller, microcomputer, programmable logic controller (PLC), application specific integrated circuit, and other programmable circuits, and these terms are used interchangeably herein.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As used herein, the terms "systems", "devices" and "apparatus" are interchangeable and include components, sub-components, sub-systems that include without limitation.

In accordance with an aspect of the disclosure a system for supplying an electrical power to a medical imaging system is provided. The system comprises a primary power supply unit for providing an input power. The system further comprises an H-bridge converter connected to the primary power supply unit and configured to receive electrical power supply from the primary power supply unit. The system further comprises at least one battery line comprising one or more batteries. The at least one battery line is connected to the H-bridge converter and the H-bridge converter is configured to charge the one or more batteries of the at least one battery line. The system further comprises an output connected to the H-bridge converter and configured to supply the electrical power stored in the one or more batteries to the medical imaging system through the H-bridge converter.

Figure 1:
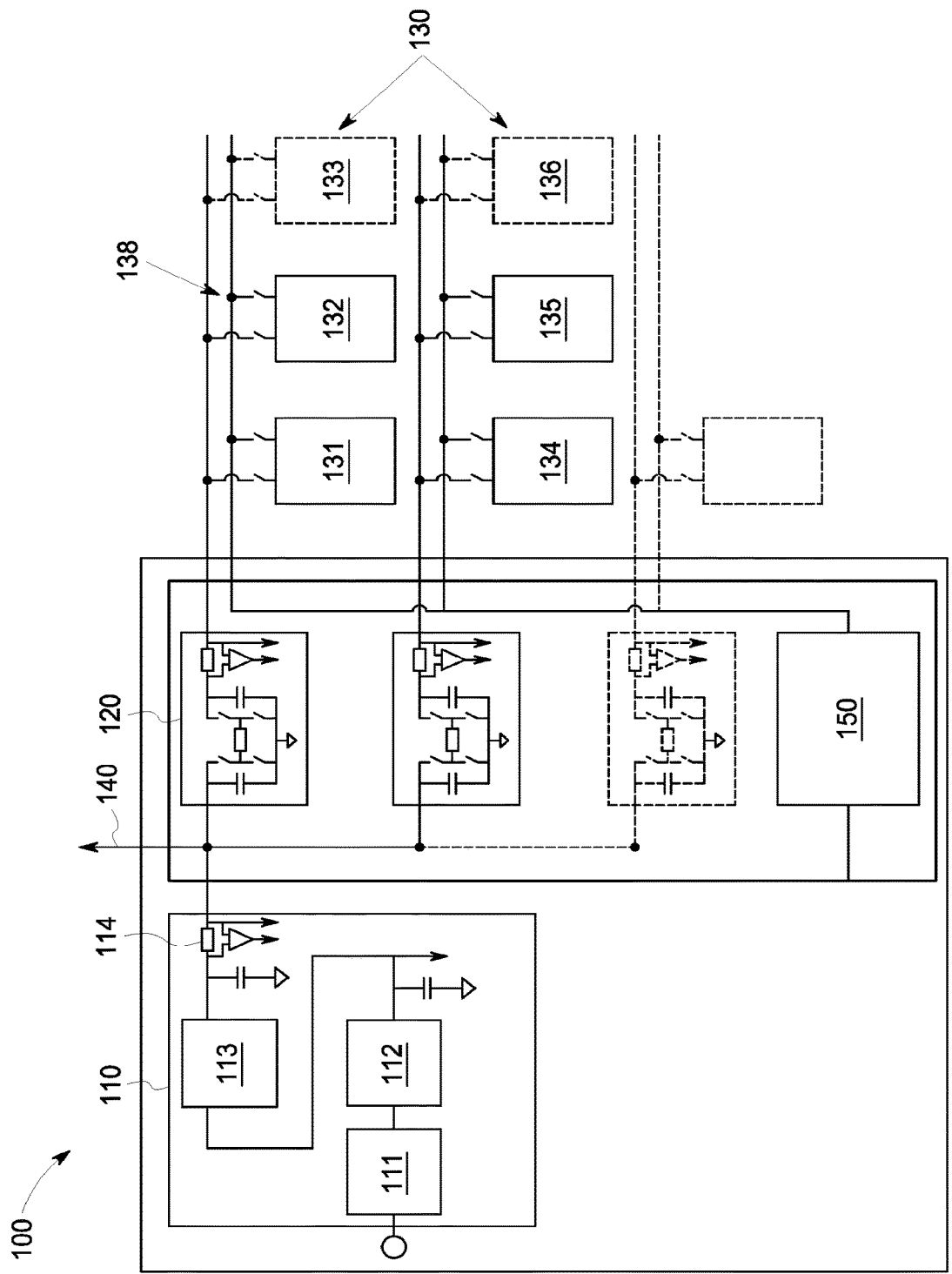
FIG. 1 illustrates a matrix battery system for supplying electrical power to a medical imaging system according to an aspect of the disclosure.

Embodiments of the present disclosure will now be described, by way of example, with reference to the figures, in which FIG. 1 shows a matrix battery system 100 for supplying electrical power to a medical imaging system (not shown). Although the system 100 is described with reference to supplying the electrical power to the medical imaging system, it is readily apparent that the system 100 may be used to supply power not only to the medical imaging systems but also for supplying power to any other kind of electrical devices. The system 100 may comprise a primary power supply unit 110 configured to receive electrical power supply from the utility. The primary power supply unit 110 may include a filter 111, a power factor correction circuit 112, a converter 113 and a first current monitoring device 114 connected in series to supply electric current to a battery line 130. The system may further comprise an H-bridge converter 120 (hereinafter H-bridge) connected to the primary power supply unit 110 for receiving the input electrical power. The H-bridge 120 may be connected to a first battery line 130 and may be used to charge the batteries (131, 132, 133) connected to the first battery line 130. Although only three batteries (131, 132, 133) have been mentioned in the present example, it is apparent that the number of batteries may be increased or decreased based on the system 100 operating conditions. The H-bridge 120 derives electrical power from the primary power supply unit 110 and uses it to charge the batteries (131, 132, 133) of the battery line 130. Although only one battery line 130 is illustrated, it is apparent that the number of battery lines 130 could be more than one and each battery line 130 may contain any number of batteries (134, 135, 136) depending on the power requirement of the medical imaging system. The one or more batteries (131, 132, 133) may be connected in parallel on the battery line 130. The charged battery lines 130 may be used to supply electrical power to the medical imaging system (not shown). During supply of the electrical power to the medical imaging systems also known as the discharging phase, the batteries (131, 132, 133) supply electrical power through the H-bridge 120 to the medical imaging system (not shown) in a direction indicated by an output 140. According to an aspect of the disclosure, the H-bridge 120 may transmit the electrical power both during the charging of the battery line 130 and discharging of the battery line 130 to supply electrical power to the medical imaging system through the output 140. Use of H-bridge 120 both to charge and discharge the battery line 130 avoids use of separate components for charging and discharging the battery line 130.

The H-bridge 120 is a known component used in the field of electrical power transmission, however, according to an aspect of the disclosure, the H-bridge 120 is provided to simultaneously charge the battery line 130 and supply electrical power to the medical imaging system (not shown) from the battery line 130 through the output 140. According to another aspect of the disclosure, more than one battery lines 130 may be connected to the output 140 and one H-bridge 120 per battery line 130 may be provided to incorporate a greater number of batteries (134, 135, 136) when the power demand from the medical imaging system increases. More number of battery lines 130 may be incorporated to provide more electrical power to the medical imaging system using one H-bridge 120 per battery line 130. This provides the necessary scalability to supply more electrical power using a greater number of batteries (131, 132 . . . n) for driving the higher system power loads.

According to an aspect of the disclosure a switching device 138 may be used to connect an individual battery (131, 132 . . . n) to the battery line 130. Use of a switching device 138 allows usage of one H-bridge 120 converter for every battery line 130 comprising more than one battery (131, 132 . . . n). This will result in a cost efficient and scaleable way to extend the battery capacity that may result in a longer system battery working time.

Figure 2:
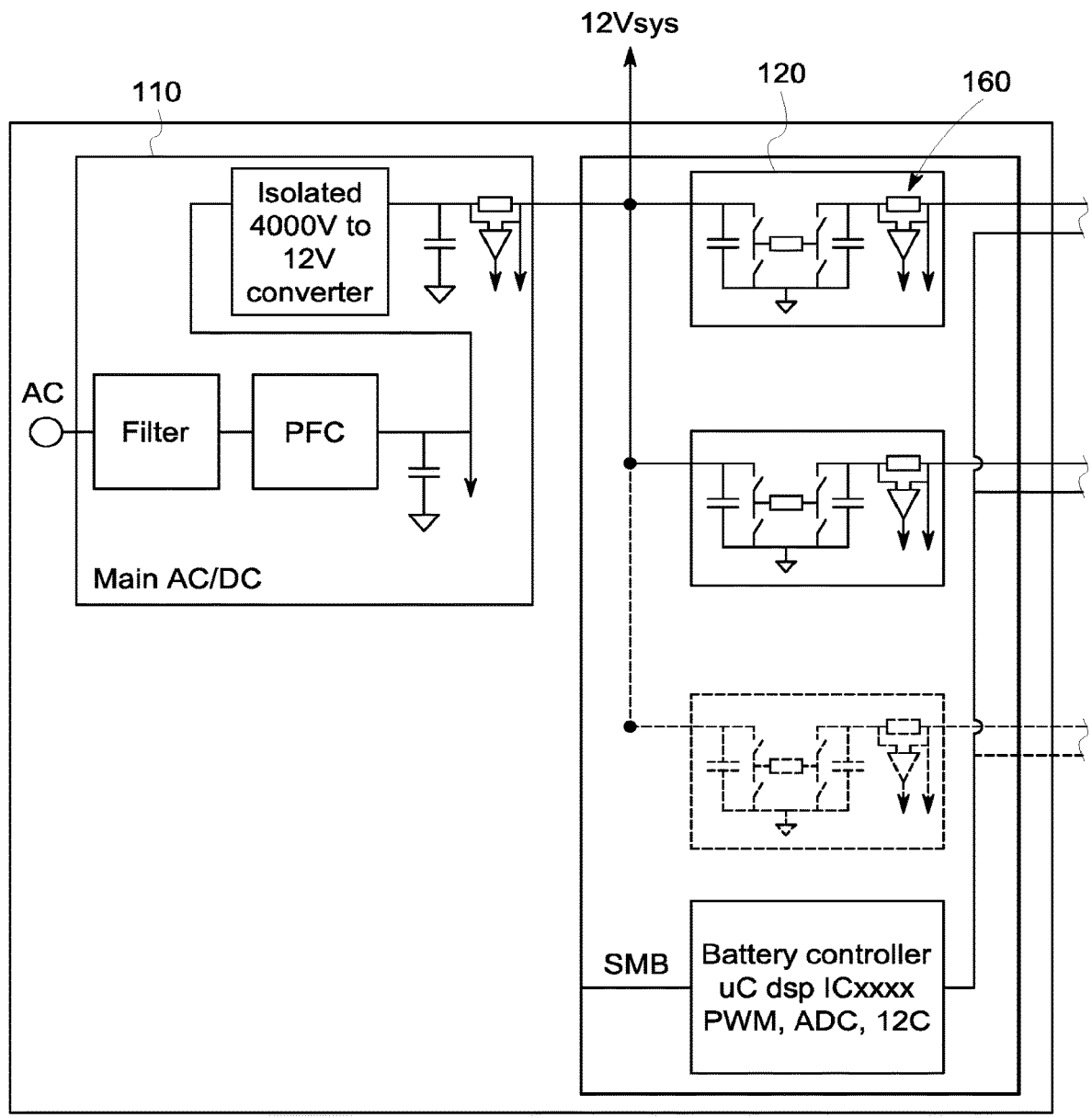
FIG. 2 illustrates an H-bridge converter structure according to an aspect of the disclosure.

According to an aspect of the disclosure, FIG. 2 shows a microcontroller 150 that may be connected to the H-bridge 120 through a second current monitoring device 160 for current measurement. The second current monitoring device 160 measures the current flowing from every battery line 120 towards the medical imaging system and sends the current value to the microcontroller 150. According to an aspect of the disclosure, referring to FIG. 1, due to discharging of the batteries, if the measured current at the second current monitoring device 160 starts falling or is less than the current required by the medical imaging system, a signal indicative of the more power requirement may be generated by the microcontroller 150 and a greater number of batteries (132, 133 . . . n) from the same battery line 130 or the other battery lines 130 may be added to supply the required electrical power. Each battery line 130 may connected to a unique current monitoring device 160, where the current and the battery parameters may be measured. All the measured current and the battery parameter values may be collected in the microcontroller 150 to regulate charging and discharging of each battery line 130 separately. By combining more than one battery lines 130 a "matrix battery system" may be generated. Use of H-bridge 120 for charging and for discharging the battery lines 130 enables using the existing components for both charging and for discharging. Compared to the conventional charge-discharge techniques, this approach enables a massive reduction of the required electrical components that reduces the main system costs.

According to an aspect of the disclosure, FIG. 1 shows connecting one or more batteries (131, 132, 133) from at least one battery line 130 to an output 140 through an H-bridge converter 120 for supplying an electrical power to the medical imaging system (not shown). For driving the higher system power loads, the system 100 may be scaleable by using more than one battery lines 130. Providing one or more batteries (131, 132, 133 . . . n) per battery line 130 and having one or more battery lines 130 makes the system "hot plug-able" and the batteries (131, 132, 133 . . . n) may be exchanged without switching off the medical imaging system. During powering of the medical imaging system, if any battery (131, 132, 133) has a defect, or the battery has reached end of the battery life stage, or the battery (131, 132, 133) is discharged, it may be replaced without shutting down the medical imaging system by plugging-in the power supply from another battery line 130 or by replacing only the individual battery (131, 132, 133) that has been discharged. Therefore, the loss of examination time for medical imaging system may be avoided and shutdown of the system 100 may not be necessary for replacing the batteries. This makes the system 100 hot-plug-able. Based on the redundant power supplies, the system 100 may be much safer against the power outages, which makes the system 100 more reliable.

The matrix battery concept allows use of the battery packs with less than 100 Wh of power for the optimized generation of the battery power solutions. The total system power and requirements for redundancy are scalable with the power and number of H-bridge battery line converters 120. Further, the redundant battery line 130 gives the advantage that each battery (131, 132, 133) can be individually charged, and discharged based on the measured system and battery parameters, which results in less thermal stress, less derating and aging of the batteries.

Figure 3:
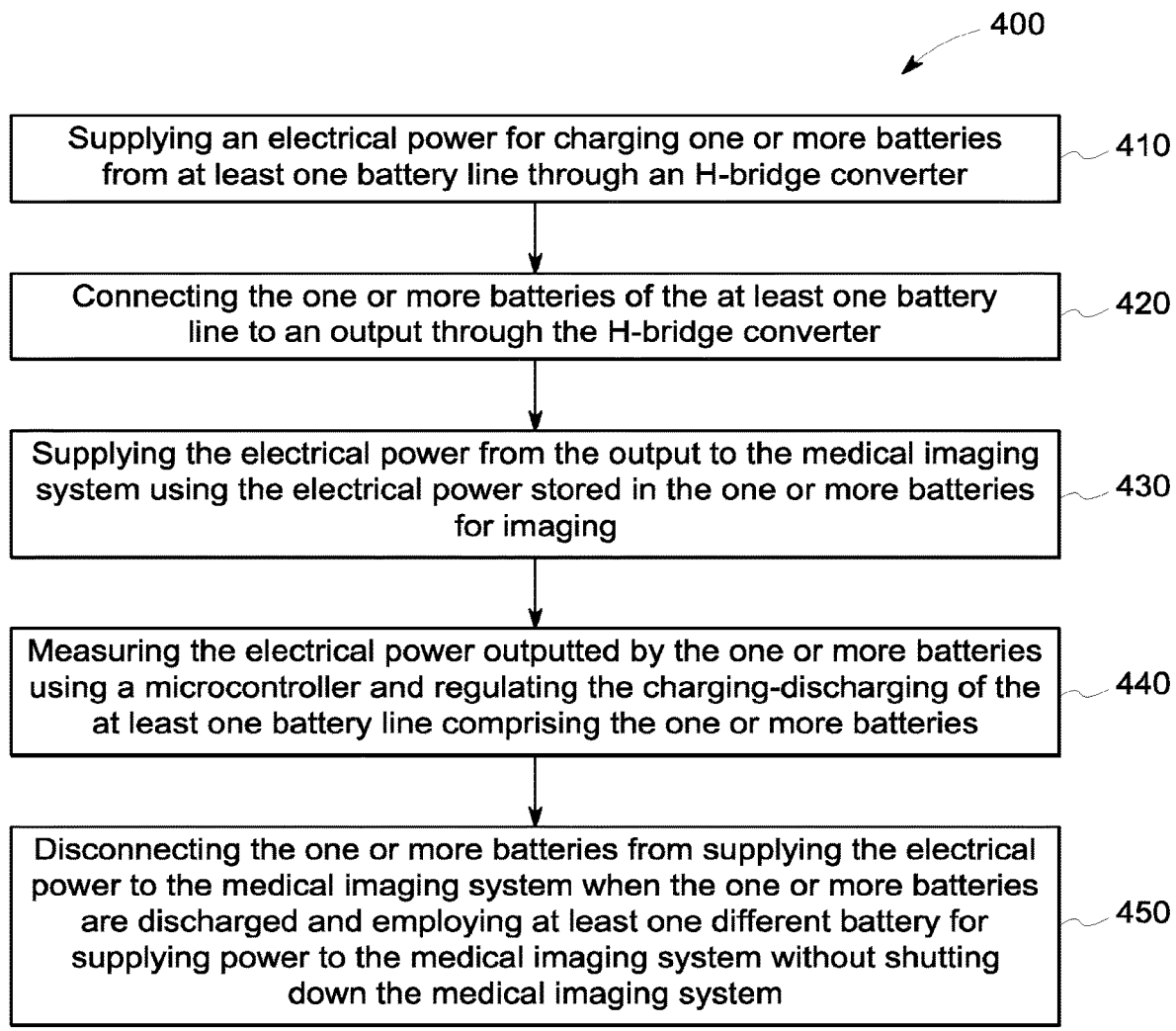
FIG. 3 illustrates a method of supplying power to a medical imaging system using the matrix battery system according to an aspect of the disclosure.

In accordance with an aspect of the disclosure, FIG. 3 shows a method 400 of supplying electrical power to a medical imaging system. The method 400 may include supplying 410 an electrical power from the primary power supply unit for charging one or more batteries (131, 132, 133) from at least one battery line 130 through an H-bridge converter 120. The method 400 further comprises connecting 420 one or more batteries (131, 132, 133) of the at least one battery line 130 to an output 140 through the H-bridge 120. The number of batteries (131, 132, 133) that may be connected to the output 140 depends on the power demand of the medical imaging system. One or more batteries (131, 132, 133) and one or more battery lines 130 comprising the one or more batteries (131, 132, 133) may be plugged-in through the H-bridge 120 if the medical imaging system requires more power for imaging. The method 400 further comprises supplying 430 an electrical power to the medical imaging system using the batteries (131, 132, 133) to carry out imaging of the subject. The method 400 further comprises measuring 440 the electrical power outputted by the one or more batteries (131, 132, 133) using a microcontroller 150 and regulating the charging-discharging of the at least one battery line 130 comprising the one or more batteries (131, 132, 133). Measuring 440 the current outputted by one or more batteries (131, 132, 133) further comprises using a second current monitoring device 160 and a microcontroller 150 to control the current being supplied by the batteries (131, 132 . . . n) to the medical imaging system. The method 400 further comprises disconnecting 450 the one or more batteries (131, 132, 133) from supplying the electrical power to the medical imaging system when the one or more batteries (131, 132, 133) has a defect, or the battery has reached end of the battery life stage, or the battery has discharged, and employing at least one different battery (134, 135, 136) for supplying the electrical power to the medical imaging system without shutting down the medical imaging system. Disconnecting 450 the one or more batteries (131, 132, 133) that has a defect, or the battery has reached end of the battery life stage, or that may have been discharged may be for recharging the batteries (131, 132, 133) without shutting down the power supply to the medical imaging system. This makes the system 100 hot-plug-able. The method 400 further comprises imaging 460 the subject using the medical imaging system.

In accordance with an aspect of the disclosure, for driving the higher system power loads, the method 400 is scale-able by using one or more battery lines 130. Providing one or more batteries (131, 132, 133 . . . n) per battery line 130 and having one or more battery lines 130 makes the system 100 "hot plug-able" and the batteries may be exchanged without switching off the medical device. During supplying 430 the power to the medical device if one or more batteries (131, 132, 133) are discharged, the method 400 comprises disconnecting 450 the one or more batteries (131, 132, 133), and recharging or replacing the batteries (131, 132, 133) without shutting down the medical imaging system. Replacing the battery may include using another battery line 130 or by replacing only the individual battery of the one or more batteries (131, 132, 133) that has been discharged. Therefore, the loss of examination time for the medical imaging system may be avoided and no shut down is needed for replacing the batteries. Based on the redundant power supplies, the method 400 is much safer against the power outages, which makes the method 400 more reliable.

The matrix battery concept allows use of the battery packs with less than 100 Wh of power for the optimized generation of the battery power solutions. The total system power and the requirements for redundancy are scalable with the power and the number of H-bridge battery line converters 120. Further, the redundant battery line 130 gives the advantage, that each battery (131, 132, 133) can be charged, and discharged individually based on the measured system and battery parameters, which results in less thermal stress, less derating and aging of the batteries.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:

1. A system for supplying electrical power to a medical imaging system, the system comprising:
   a primary power supply unit;
   an H-bridge converter connected to the primary power supply unit and configured to receive electrical power from the primary power supply unit;
   at least one battery line comprising a plurality of batteries, wherein the at least one battery line is connected to the H-bridge converter and the H-bridge converter is configured to provide electrical power to the plurality of batteries for charging the plurality of batteries; and
   an output connected to the H-bridge converter and configured to supply electrical power stored in the one or more batteries to the medical imaging system through the H-bridge converter,
   wherein the H-bridge converter comprises two sets of two switches, the two switches in each set being connected in series, the two sets of switches being connected in parallel,
   wherein the plurality of batteries are connected in parallel and are configured to be exchanged without switching off the medical imaging system.

2. The system of claim 1, further comprising at least one switch configured to connect each of the plurality of batteries to the at least one battery line.

3. The system of claim 1, further comprising a microcontroller connected to the H-bridge converter through a current monitoring device, wherein the current monitoring device is configured to measure a current value of electrical power outputted by the plurality of batteries, send the current value to the microcontroller, and wherein the microcontroller is configured to regulate charging-discharging of the plurality of batteries based on the current value.

4. The system of claim 1, wherein the plurality of batteries are disconnected from the at least one battery line when the plurality of batteries are discharged, and wherein the system further comprises at least one different battery employed to supply power to the medical imaging system without shutting down the medical imaging system.

5. The system of claim 1, wherein the at least one battery line is disconnected from the H-bridge converter when the at least one battery line is discharged and wherein the system further comprises at least one additional battery line employed to supply electrical power to the medical imaging system without shutting down the medical imaging system.

6. The system of claim 5, further comprising at least one additional H-bridge converter connected to the least one additional battery line to supply electrical power to the medical imaging system.

7. The system of claim 1, wherein the plurality of batteries are lithium-ion batteries with a power capacity of 100 Wh.

8. The system of claim 1, wherein a number of the plurality of batteries connected to the output to supply electrical power to the medical imaging system is varied based on a power demand of the medical imaging system.

9. The system of claim 8 wherein the number of the plurality of batteries connected to the output is increased when the power demand from the medical imaging system increases and the number of the plurality of batteries connected to the output is decreased when the power demand from the medical imaging system decreases.

10. The system of claim 1 wherein the plurality of batteries are connected in parallel on the at least one battery line.

11. A method for supplying electrical power to a medical imaging system, the method comprising:
   supplying electrical power from a primary power supply unit for charging plurality of batteries connected to at least one battery line through an H-bridge converter and storing electrical power in plurality of batteries;
   connecting the plurality of batteries of the at least one battery line to an output through the H-bridge converter;
   supplying electrical power from the plurality of batteries to the medical imaging system through the H-bridge converter and the output; and
   exchanging one of the plurality of batteries while the medical imaging system remains powered on,
   wherein the H-bridge converter comprises two sets of two switches, the two switches in each set being connected in series, the two sets of switches being connected in parallel.

12. The method of claim 11 further comprising:
   measuring electrical power outputted by the plurality of batteries using a current measuring device connected to a microcontroller; and
   regulating the charging-discharging of the at least one battery line comprising the plurality of batteries by the microcontroller.

13. The method of claim 11 further comprising disconnecting the plurality of batteries from supplying electrical power to the medical imaging system when the plurality of batteries are discharged and employing at least one different battery for supplying power to the medical imaging system without shutting down the medical imaging system.

14. The method of claim 11 further comprising disconnecting at least one battery line from powering the medical imaging system when the at least one battery line is discharged and employing at least one additional battery line for powering the medical imaging system without shutting down the medical imaging system.

15. The method of claim 14 further comprising connecting an additional H-bridge converter to the least one additional battery line for supplying electrical power to the medical imaging system.

16. The method of claim 11, wherein supplying electrical power to the medical imaging system using the plurality of batteries comprises varying a number of the plurality of batteries connected to the output based on a power demand of the medical imaging system.

17. The method of claim 16 wherein varying the number of the plurality of batteries connected to the output based on the power demand of the medical imaging system comprises increasing the number of the plurality of batteries connected to the output when the power demand from the medical imaging system increases, and decreasing the number of the plurality of batteries connected to the output when the power demand from the medical imaging system decreases.

18. The method of claim 11 further comprising employing at least one switch for connecting each of the plurality of batteries to the at least one battery line.

19. The system of claim 1, wherein the H-bridge converter further comprises a current monitoring device connected between the two sets of switches, the current monitoring device being connected to each set of switches between the two switches in the set.

* * * * *